United States Patent [19]

Fowler, Jr.

[11] Patent Number: 5,728,041
[45] Date of Patent: Mar. 17, 1998

[54] ISOLATOR FOR USE IN SURGERY OR AS A CLEAN ROOM AND METHOD OF USING THE SAME

[75] Inventor: James M. Fowler, Jr., Houston, Tex.

[73] Assignee: Lone Star Medical Products, Inc., Houston, Tex.

[21] Appl. No.: 628,554

[22] Filed: Apr. 10, 1996

[51] Int. Cl.$^6$ .......................... A61G 10/00; A61G 10/02
[52] U.S. Cl. ........................................................ 600/21
[58] Field of Search ........................... 600/21, 22; 312/1, 312/3–6

[56] References Cited

U.S. PATENT DOCUMENTS

| | | |
|---|---|---|
| 2,473,033 | 6/1949 | Letac . |
| 3,265,059 | 8/1966 | Matthews . |
| 3,272,199 | 9/1966 | Matthews . |
| 3,763,857 | 10/1973 | Schrading . |
| 3,850,172 | 11/1974 | Cazalis . |
| 4,026,286 | 5/1977 | Trexler . |
| 4,161,172 | 7/1979 | Pickering . |
| 4,275,719 | 6/1981 | Mayer . |
| 4,304,224 | 12/1981 | Fortney ............................. 600/21 |
| 4,328,793 | 5/1982 | Martin . |
| 4,367,728 | 1/1983 | Mutke . |
| 4,485,806 | 12/1984 | Akers ............................. 600/21 |
| 4,550,713 | 11/1985 | Hyman . |
| 4,581,538 | 4/1986 | Lenhart . |
| 4,612,916 | 9/1986 | Akers et al. ............................. 600/21 |
| 4,865,049 | 9/1989 | Gatti . |
| 4,867,177 | 9/1989 | Urheim . |
| 4,950,222 | 8/1990 | Scott et al. . |
| 5,047,072 | 9/1991 | Wertz et al. ............................. 604/20 X |
| 5,342,121 | 8/1994 | Koria ............................. 600/21 X |

OTHER PUBLICATIONS

*Lasers in Surgery and Medicine*, 8: 248–253 (1988) "Protection of the Rat Lung from the Harmful Effects of Laser Smoke", Baggish, M. S., et al.

*American Journal of Surgery*, 104: 891–899 (1962), "A Plastic Isolator for Operating in a Sterile Enviroment", Levenson, S. M., et al.

*British Medical Journal*, 1: 322–324 (1974) "New Inventions: The Surgical Isolator", McLauchlan, J., et al.

*Journal of the American Medical Association*, vol. 259, No. 8, pp. 1199–1202, "Papillomavirus in the Vapor of Carbon Dioxide Laser–Treated Verrucae", Garden, J. M., et al.

*Roche Medical Image*, vol. 3 No. 3 Autumn 1961, "Clinical Vistas for Germ–free Research".

Primary Examiner—Jennifer Bahr
Assistant Examiner—Samuel Gilbert
Attorney, Agent, or Firm—Vaden, Eickenroht & Thompson, L. L. P.

[57] ABSTRACT

An isolator and method of using same for providing an atmosphere free of contamination from external sources and for containing and evacuating contaminates generated during the course of a surgical procedure, particularly laser procedures that are performed within the isolator. The isolator includes a double chambered structure made of a flexible material on a rigid frame. Filtered air is provided to the outer chamber and enters the inner chamber through various openings in the inner enclosure walls. The inner chamber is under negative pressure and the mix of filtered air and any air borne contaminants generated by the procedure are evacuated to an air handling unit where contaminants are neutralized and removed from the air. A portion of the top side of the bag is made of a relatively stiff, optically transparent, material through which the surgeon or the assembly worker can view the work area. A plurality of open-ended sleeves are attached to the bag through which the hands are arms of the surgeon and his assistants or the worker can extend into the work space.

20 Claims, 3 Drawing Sheets

ISOLATOR FOR USE IN SURGERY OR AS A CLEAN ROOM AND METHOD OF USING THE SAME

BACKGROUND

Many surgical procedures that are now being performed are known to generate air-borne particles that may have viral or bacterial contamination. If not properly contained, the operating room and surgical personnel present during these procedures are exposed to such contamination. This problem is particularly acute in the case of laser surgical procedures where a plume of material may include patient tissue and fluids as well as smoke and other gases. This invention relates to the containment and neutralization of such air-borne contaminants by creating a barrier of filtered air between the local area of the surgical procedure and the surgical personnel, patient, and operating room environment. Further, it is anticipated that the method and apparatus of this invention will find uses outside of the medical field such as with the assembly and servicing of equipment that is sensitive to environmental contamination.

Although medical science and technology is growing at an exponential rate, the ability of surgical procedures and other medical treatments to cure is impeded by our inability to prevent infection. Common procedures which have been used to minimize the risk of infection include the sterilization of all instruments and materials which come in contact with the wound, chemically sterilizing the patient's skin at the site of the procedure, and thoroughly scrubbing the surgical team before donning sterilized caps, gowns, masks and gloves. In addition, the air in the operating room air is constantly changed and filtered. Nevertheless, even when these precautions and others are taken, a significant percentage of supposedly clean operations result in wound infections.

One of the problems is that disease organisms are ubiquitous in the operating room air, on the skin, and in the respiratory and gastrointestinal tracts of the patient and every other person in the room. For example, it has been determined that 30,000 to 60,000 particles are shed each minute from each person in the operating room. Bacterial contaminants are released into the atmosphere from the skin, by breathing and passing gas, and from the urinary tracts of those present. Further, potentially infectious particles or organisms fall from the hair, and pass through damp gowns and masks and through punctured gloves to create additional hazards of contamination and infection.

While improved methods for preventing contamination and infection are being found, it is becoming increasing clear that even the most minor exposure to contaminants may be sufficient to generate infection or spread disease. More particularly, there are certain types of surgical procedures that experience a higher than normal rate of infection, such as the implantation of prosthetic devices or artificial organs. The dose of bacteria necessary to invade the wound and cause an infection is reduced when foreign matter, such as an implanted device, is introduced into the body. Repeated experimental and clinical studies have proven that the mere presence of a foreign body can seriously impede the human body's immune system. Over 50,000 bacteria may be required to cause a surgical wound infection in normal operations whereas only 100 bacteria can cause infection when an implant device, even though inert, is introduced. In some implant surgical procedures, it has been theorized that a single bacterium may be all that is necessary to cause a deep wound infection.

In the case of laser surgical procedures, the risk of contamination is compounded by the generation of a laser plume containing smoke and other debris during the operation. Further, the added risk of contamination due to this plume is not limited to contamination of the wound site of the patient. Due to its air borne nature, if this plume is not contained and evacuated from the area around the wound site, such air-borne contaminants may settle on any exposed surface in the operating room as well as in the eyes and the respiratory tracts of the patient and surgical personnel.

The most common type of laser device being used in surgical procedures is a $CO_2$ laser emitting at a wavelength of just under 11,000 nanometers. During its use, the energy of this laser is absorbed by cellular water causing it to be heated and vaporized, and ultimately causing cells to rupture. This vaporization creates a plume of materials that can include water, smoke, and other gases, carbonized cell fragments, cellular, or viral DNA, and in some cases live cells and active viruses. With increased awareness of such highly communicable diseases such as AIDS, such contamination by such air borne materials is highly undesirable.

Therefore it is an object of this invention to provide a double chambered surgical isolator in which surgical procedures may be performed and which will contain any smoke and airborne particles generated by that procedure, and an air handling unit which is capable of maintaining a flow of clean filtered into the surgical isolator, evacuating smoke and airborne particles, and cleansing the evacuated air for recirculating it back into the surgical isolator.

The surgical isolator is composed of an inner enclosure and chamber in which the surgical procedure is carried out and an outer enclosure and chamber enveloping the inner enclosure. The air-handling unit provides filtered air to the outer chamber while simultaneously evacuating air from the inner chamber such that positive pressure is maintained in the outer chamber while a negative pressure is maintained in the inner chamber. Any leakage in the walls of the inner enclosure will result in a flow of clean filtered air from the outer to the inner chamber. Any leakage in the walls of the outer enclosure will result in a flow of clean filtered air into the operating room. Inner enclosure walls are provided with openings through which filtered air passes into the inner chamber from the outer chamber. Arm ports are provided in both the inner and outer enclosure walls to allow surgical personnel to perform the procedure on the patient. Attached at the periphery of the arm ports are tapered sleeves with elastic bands, such that when the sleeve is not in use, the flow of air through the sleeve is restricted.

An instrument lock, attached to the outer enclosure, is provided with removable doors to the inner chamber and to the operating room environment respectively. The door separating the instrument lock from the inner chamber is provided with openings to allow a flow of filtered air from the outer chamber into the instrument lock and from the instrument lock into the inner chamber. Instruments required during the procedure may be introduced into the inner chamber through the instrument lock either before or during a surgical procedure.

The air handling unit of this invention is capable of providing a flow of filtered air to the outer chamber while simultaneously evacuating smoke and contaminated air from the inner chamber. The air handling unit is equipped with means for neutralizing any viruses or bacteria present in the smoke or airborne particles and with appropriate filters for removing all such particles from the air so that it can be recycled back into the outer chamber.

It is a further object of this invention to provide a method for isolating a wound site and any airborne contaminants generated at that site from the patient and surgical personnel by first enclosing the site within an inner chamber, enveloping the inner chamber within an outer chamber, providing openings between the inner and outer chambers, introducing a stream of filtered air into the outer chamber in order to inflate the outer chamber and to maintain a steady flow of filtered air into the inner chamber, and simultaneously evacuating air from the inner chamber.

It is a further object of the method of this invention to eliminate any live cellular or active viral matter that may be present in the air, to filter the air evacuated from the inner chamber, and to recirculate the filtered air into the outer chamber.

Previous means of containing a plume generated during laser surgical procedures have varied from systems where the entire patient is enclosed within an isolation unit to more simple systems where a vacuum is positioned close to the wound site. The former systems are generally too bulky and too complicated to set up and use for simple procedures. The value and emphasis of many laser procedures is in the simplicity and speed with which many minor operations can be performed using a laser device. These benefits are lost where the entire patient and/or surgical personnel must be enclosed in an isolator in order to perform the operation.

In the case of the more simple evacuation systems, although various structures have been devised for directing the plume toward an evacuation inlet, the inlet must be held very close to the surgical field in order to maximize containment of the gases and other debris that are generated. Because of its proximity to the surgical field, the evacuation inlet may interfere with the performance of the procedure and commonly becomes clogged by surgical sponges, cotton or gauze which is inadvertently sucked from the field. Any fluids or other materials that are sucked into an evacuator may damage the vacuum and shorten its life.

U.S. Pat. No. 4,998,538 issued Mar. 21, 1991 and entitled, "Medical Drape for Laser Surgery," is an example of a device which encloses the wound site within a surgical drape and an evacuation system for removing laser plume from the enclosure. However, the device of the '538 patent simply maintains a negative pressure within the region enclosed by the drape. The drape is not air tight or sealed. In fact, the disclosure provides that slits or openings may be provided in the walls of the enclosure. The result of this design is that the wound will be exposed to unnecessary contamination as air is drawn into the enclosure from the operating room across the wound.

It is a further object of this invention to provide a barrier of filtered air between the site of the wound and the patient and surgical personnel which protects the wound from contamination by any airborne contaminants present in the operating room while simultaneously protecting the patient and surgical personnel from exposure to any air-borne contaminants generated during the surgical procedure.

It is a further object of this invention to provide an isolator which is easily assembled, encloses only the surgical site and wound of the patient and which contains and evacuates all of the air-borne materials produced during a laser procedure but does not interfere with the performance of the operation.

It is a further object of this invention to provide an isolator which is simple and inexpensive to manufacture such that it may be disposed of following a single use.

The objects and advantages of the isolator of this invention in solving the problems of infections and containment in surgical procedures have been described above. The isolator of this invention also has utility in industry. It can replace the "clean rooms" now used to provide contamination free atmosphere in which equipment is assembled that is especially sensitive to environmental contamination such as dust. A typical clean room has an atmospheric-control system that rigidly controls temperature and humidity and bars entrance, by means of filters, of all but the tiniest mote of dust. Walls and ceilings are of one piece plastic with no cracks where dust might collect and are washed and vacuumed daily. Maintenance cannot be done within the room: plumbing, wiring, and lighting are so arranged that lighting can be handled in crawl spaces above the ceiling. The rooms typically have no sharp corners; they are rounded off to forestall dust collection.

Before entering, workers don special clean suits, including head covering and boots, and pass under an "air shower" that removes all loose particles of matter. The parts that make up the assembly are thoroughly cleaned and polished before delivery to the clean room, which they enter through an air lock.

With the isolator of this invention, much of the elaborate equipment, special room design, and special clean suits can be eliminated greatly reducing the cost of a clean room operation.

These and other objects, advantages and features of this invention will be apparent to those skilled in the art from a consideration of this specification, including the attached drawings and appended claims.

Figures 1, 2:
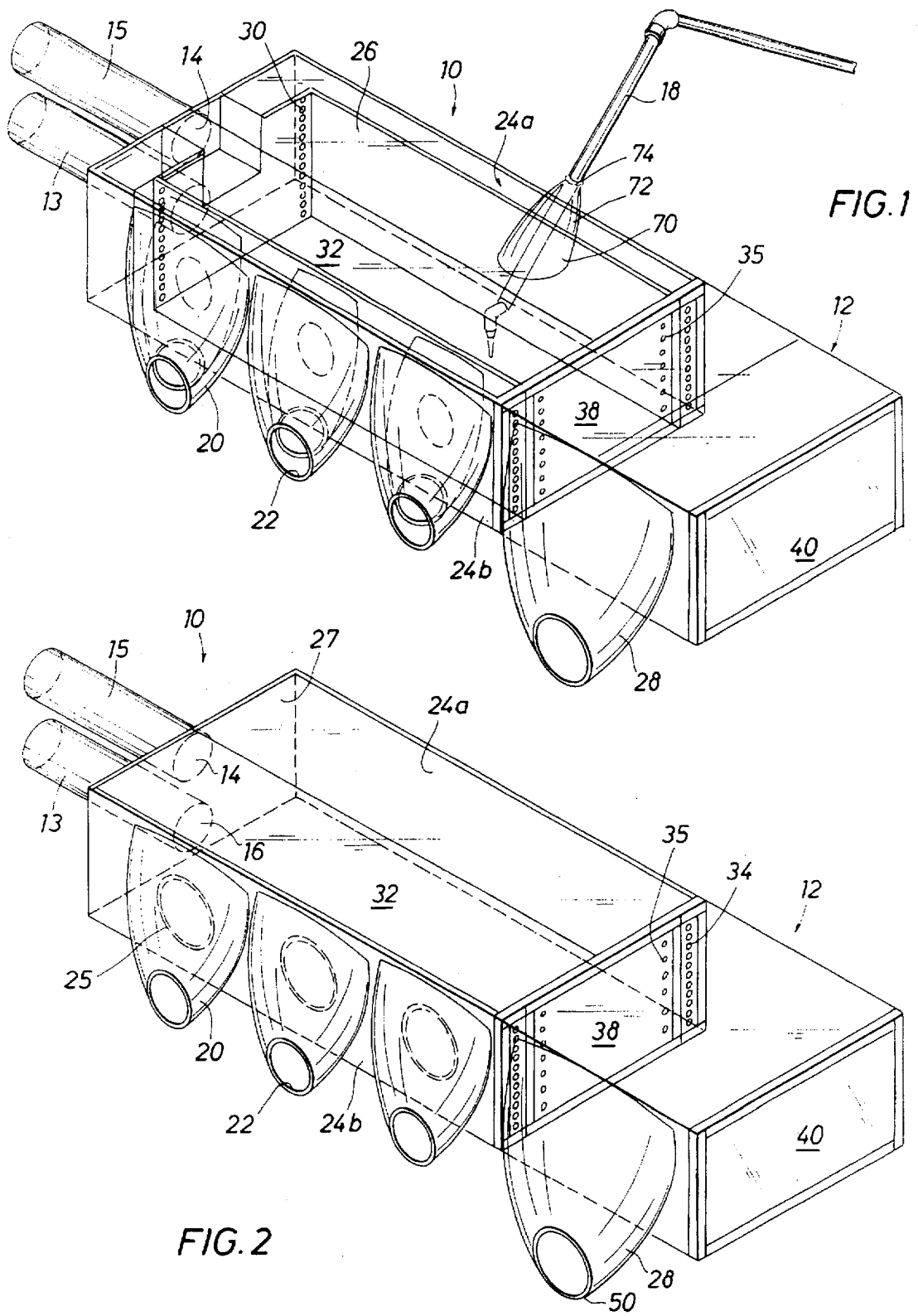
FIG. 1 is a perspective view of the isolator of this invention showing the assembled inner and outer enclosures, an attached instrument lock and a segment of a laser device for performing a laser surgical procedure.
FIG. 2 is a perspective view of the outer enclosure alone.

The isolator shown in the drawings is described below as it is used in a surgical procedure. As explained above, it can be used as a clean room for industrial purposes equally as well.

The isolator shown in FIGS. 1–5 and generally indicated by the number 10, is essentially a double enclosure structure having a rigid frame covered with a transparent flexible material. The isolator is made of materials through which disease organisms and matter cannot pass. Most of the walls in the preferred embodiment of the structure are made of a clear, flexible acrylic resin plastic with the exception of the optical window 32 in the top portion of the isolator. Window 32 is made out of a relatively stiff, optically clear, plastic material, such as the thermoplastic carbonate linked polymer produced by reacting bisphenol A and phosgene and sold under the trademark "Lexan" by the General Electric Co. This material provides the surgical team with a clear, undistorted, view of the wound site.

Isolator 10 is prepared for use in surgical procedures by first assembling the inner enclosure around the surgical site.

Figure 3:
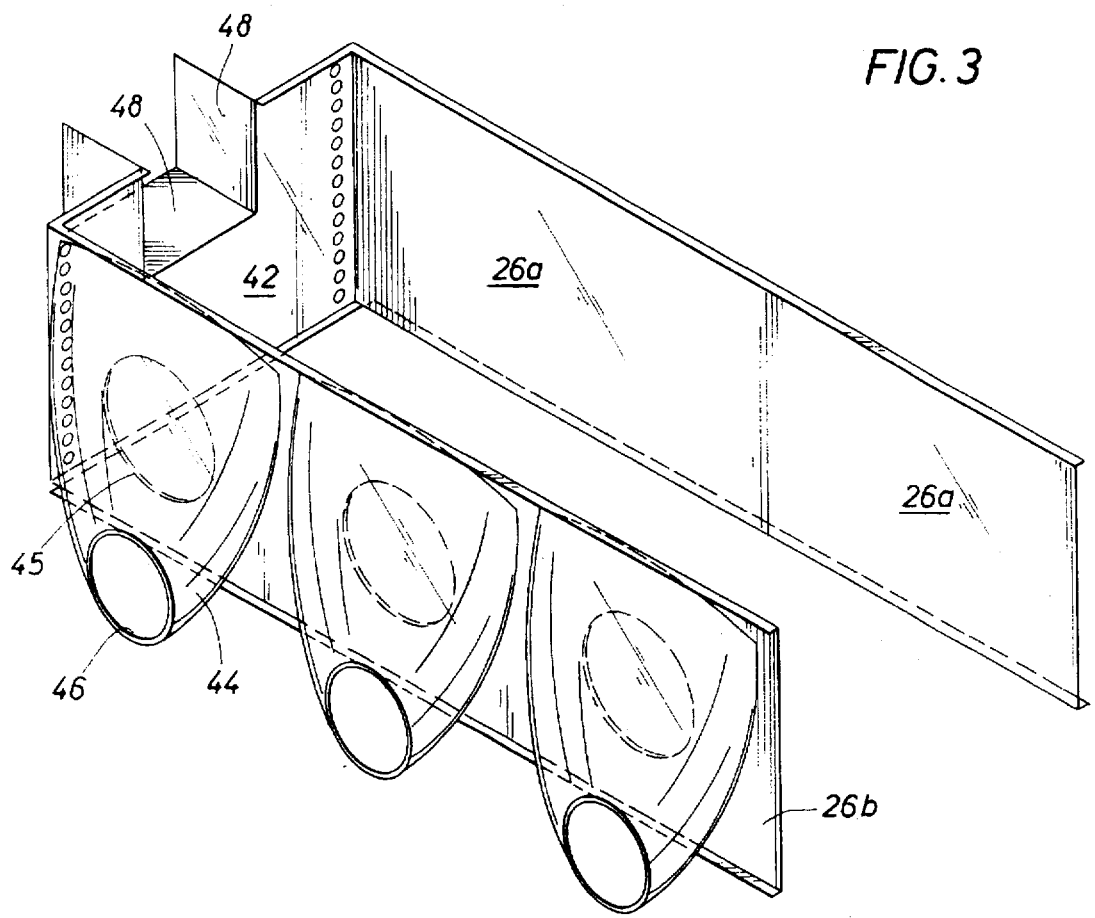
FIG. 3 is a perspective view of the inner enclosure alone.

In FIG. 3, side walls 26a and 26b are connected to one other by end wall 42 and are positioned around the surgical field. End wall 42 is provided with openings 30 to allow the passage of air into the inner chamber and with extension 48 for the evacuation connection with the air handling unit. Side wall 26b is provided with armports 45 and with a sleeve 44 attached about the periphery of each armport 45. Sleeves 44 are provided with elastic bands for gathering the ends of the sleeves together in order to restrict the flow of air through the sleeve when it is not in use. Any leakage through an armport will result in a flow of filtered air from the outer chamber to the inner chamber due to the pressure differential that is maintained by the air handling unit. Side wall 26a may likewise be provided with armports 45 but are not shown as such in FIG. 3.

Figure 4:
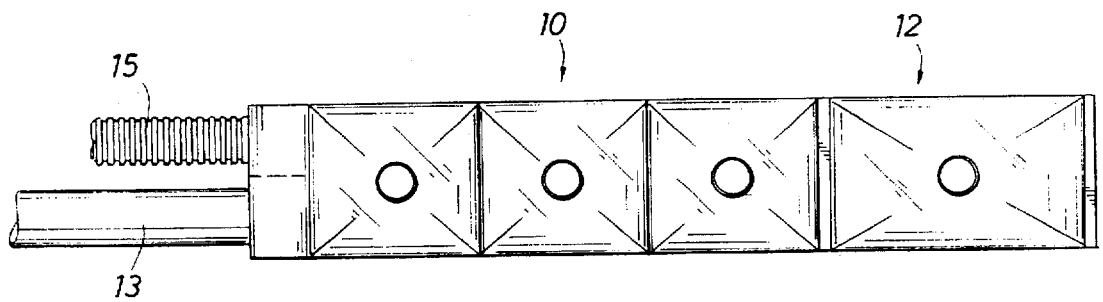
FIG. 4 is a side view of the isolator of this invention showing the conduits to the air handling system, the sleeved side openings and the attached instrument lock.
Figure 5:
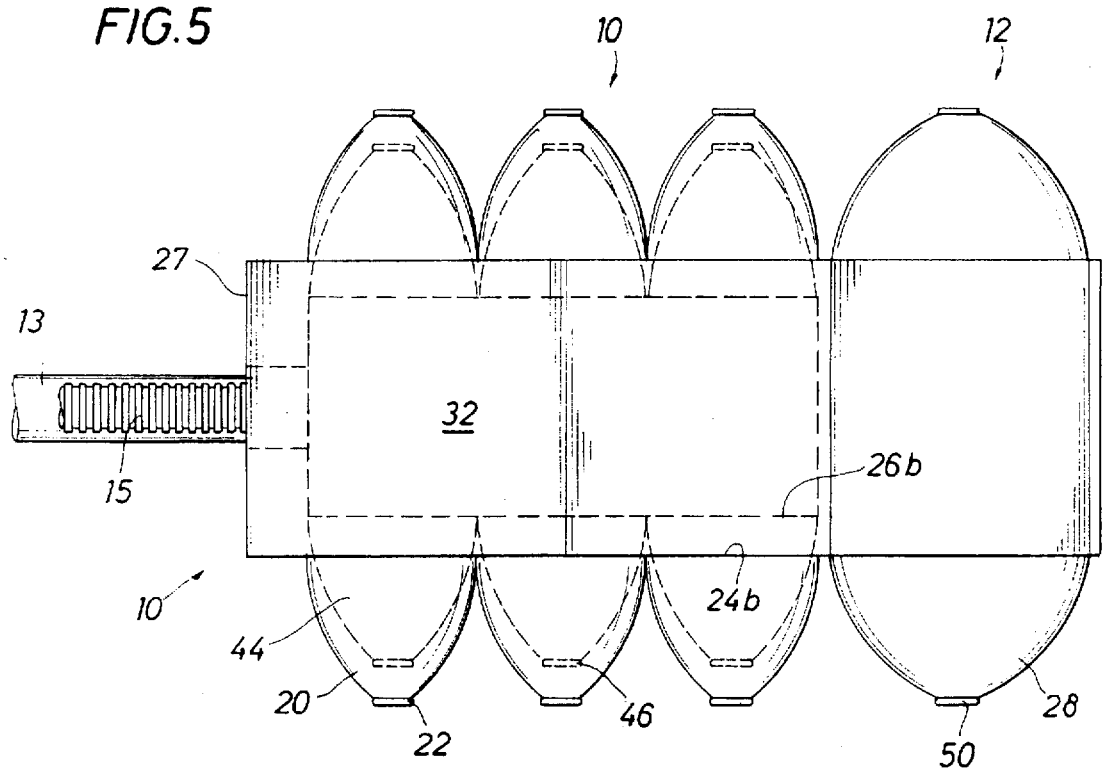
FIG. 5 is a top view of the isolator of this invention showing the conduits to the air handling system, the sleeved side openings and the attached instrument lock.
Figure 6:
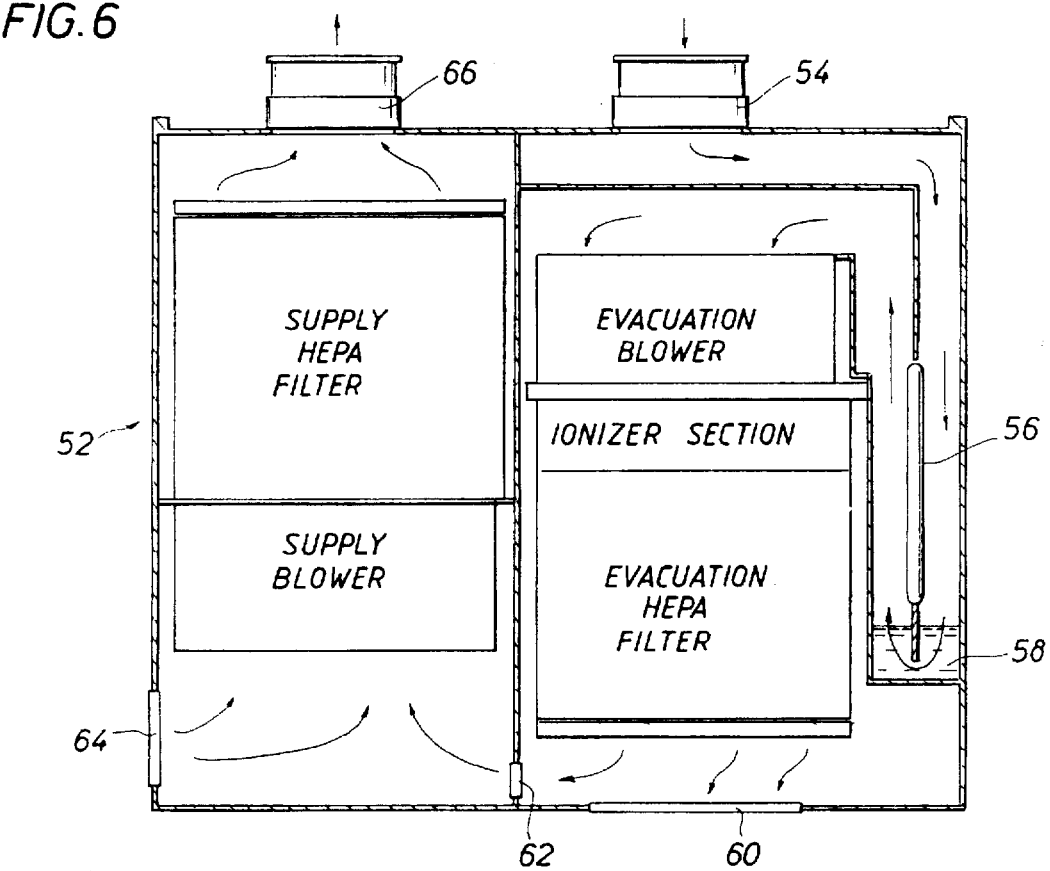
FIG. 6 is a schematic representation of a cross section of the air handling system of this invention with arrows to indicate the direction of air flow through the system.

Once the inner enclosure is positioned around the surgical field the outer enclosure is assembled around that inner enclosure. As shown in FIGS. 1, 2, and 4, side walls 24a and 24b are positioned around the inner enclosure and are connected by endwall 27. Endwall 27 is provided with filtered air inlet 16 for connecting to the air handling unit 52 for introducing filtered air into the outer chamber. Endwall 27 is also provided with evacuation outlet 14 for connecting to the air handling unit 52 for withdrawing contaminated air from the inner chamber via extension 48.

As shown in FIG. 1, instrument lock 12 is attached at the distal end of side walls 24s and 24b. Instrument lock 12 is separated from the inner chamber by removable door 38. Door 38 is connected to side walls 26a and 26b of the inner enclosure and side walls 24a and 24b of the outer enclosure. Further, door 38 is provided with openings 34 to allow for the flow of filtered air out of the outer chamber and into the instrument lock 12, and with openings 35 to allow the air to flow from the lock into the inner chamber. Instrument lock 12 is further provided with removable door 40 which separates the interior of the lock from the rest of the operating room. For the alternative embodiment where no instrument lock is utilized, door 38 is eliminated and door 40 will connect with side walls 24a and 24b and with side walls 26a and 26b to separate the isolation unit from the operating room.

Connected to side walls 24a and 24b are armports 25 which are aligned with armports 45 on the side walls of the inner enclosure so that surgical personnel may extend their hands and arms through to work within the inner chamber. Sleeves 20 are provided on the side walls attached about the periphery of armports 25. Further, sleeves 20 are provided with elastic bands or gatherings 22 at the end of each sleeve to restrict the flow of air out of the sleeve when it is not in use. Any leakage through armports 25 will result in a flow of filtered air out of the arm ports into the operating room due to the relatively high pressure in the outer chamber.

Isolator 10 is provide with a relatively rigid, transparent window 32 which allows the surgical personnel a clear view of the procedure without distortion or obstruction. As shown in FIG. 1, window 32 is provided with laser port 70 for laser device 18 to be introduced into the inner chamber. Port 70 is provided with sleeve 72 attached about its periphery, and which is gathered around the extension of the laser device by elastic band 74. Port 70 should be relatively small so as not to obstruct the view of the surgical field, but should not be so small as to restrict the movement of laser device 18 within the inner chamber.

Once the isolator has been assembled around the surgical field, conduits 13 and 15 are attached to the air handling unit. When in operation, air handling unit 52 provides a stream of filtered air into the outer chamber while evacuating air from the inner chamber. To follow the air flow from the air handling unit, filtered air is pumped though conduit 13 and through air inlet 14 on outer enclosure end wall 27. The air enters the outer chamber providing positive pressure to this chamber. Leakage out of outer chamber occurs at armports 25 to the operating room, armports 45 to the inner chamber, through openings 30 on inner enclosure end wall 42 and through openings 35 on instrument lock door 38. These latter points of leakage represent the means by which filtered air is introduced into the inner chamber. In the inner chamber, smoke, gases and other airborne materials being generated by the procedure are mixed with the filtered air from the outer chamber and are evacuated out of the inner chamber through extension 48 and through evacuation outlet 14.

The air handling unit 52 is divided into evacuation and supply sections. In the evacuation portion of the unit, contaminated air from the inner chamber is evacuated via evacuation conduit 15 by the evacuation blower. Conduit 15 is connected to the air handling unit's housing and channels the contaminated air into the housing through contaminated air inlet 54. The air and any suspended matter are exposed to ultraviolet radiation from UV lamp 56 in order to neutralize any live cellular or active viral matter that may be present in the evacuated air. Preferably, UV lamp 56 has a surface area of at least 10 square inches and emits radiation at a wavelength of 254 nanometers. An alternative means for neutralizing any live cellular or active viral matter that may be present is to bubble the air and contaminants through a solution containing a biocide and/or virucide.

The neutralized air is then drawn through the evacuation blower and is blown through an ionizer in order to charge any particulate matter that may be suspended in the air. The air and any charged particles are then passed through a high efficiency particulate (HEPA) filter which is preferably 12"×12"×12". By placing a charge on the particles and then grounding the aluminum separators of the HEPA filter, the efficiency of the HEPA filter will be enhanced such that submicron sized particles will be trapped. The air leaving the evacuation HEPA filter may be directed to the supply side of the air handling system through recirculation control valve 62, or may be discharged to ambient air through discharge outlet 60.

If recirculated, the filtered air is combined with additional ambient air that is supplied through make-up air inlet 64. The combined air is then drawn through the supply blower and passed through a supply HEPA filter to filter out any contamination present in the ambient air. The air is then forced out of the air handling system through filtered air supply outlet 66 and directed through supply conduit 15 to the outer chamber. Although not shown, air handling system 52 is preferably controlled by separate volume or speed controls for the evacuation and supply blowers as well as with indicators to monitor the operation of the blowers and the ultraviolet lamp and ionization chamber.

From the foregoing it will be seen that this invention is one well adapted to attain all of the ends and objects hereinabove set forth, together with other advantages which are obvious and which are inherent to the apparatus and structures.

It will be understood that certain features and subcombinations are of utility and may be employed without reference to other features and subcombinations. This is contemplated by and is within the scope of the claims.

Because many possible embodiments may be made of the invention without departing from the scope thereof, it is to be understood that all matter herein set forth or shown in the accompanying drawings is to be interpreted as illustrative and not in a limiting sense.

What is claimed is:

1. A surgical isolator for protecting the patient and medical personnel from airborne contaminants produced during laser surgery and other surgical procedures comprising an inner enclosure which is adapted to be positioned around the surgical field on the patient forming an inner chamber, an outer enclosure having an upper surface surrounding the inner chamber, a plurality of openings in each enclosure, the openings of the inner enclosure aligned with the openings in the outer enclosure, a plurality of open-ended sleeves attached to the outer enclosure through which medical personnel can extend their hands through the sleeves and the openings into the inner chamber, each sleeve having an elastic band adjacent the end open end of the sleeve adapted to grip the arm extending through the opening and restrict the flow of air from the inner, and outer chambers through the open end of the sleeve, an exhaust fan and exhaust line connected to the inner enclosure for drawing air and entrained contaminated particles produced by the surgery out of the inner chamber through the exhaust line, openings in a wall of the inner enclosure, and a supply blower for supplying the outer chamber with air at a pressure above the pressure in the inner chamber to insure that air flows from the outer chamber to the inner chamber so that entrained contaminated particles produced by the surgery are confined to the inner chamber and are carried out of the inner chamber by the exhaust fan.

2. The surgical isolator of claim 1 further provided with a plurality of inner open-ended sleeves of flexible material having one end attached to the inner enclosure with each sleeve surrounding an opening in the inner enclosure so that medical personnel can extend an arm through an outer and an inner sleeve and into the inner chamber.

3. The surgical isolator of claim 1 in which a portion of the upper surface of the outer enclosure is made of a relatively stiff optically transparent material to allow a clear view of the procedure being conducted in the inner chamber.

4. The surgical isolator of claim 1 further provided with an instrument lock at one end of the isolator, the instrument lock having a first door between the lock and the inner chamber, openings in the door through which air from the outer chamber can flow into the lock and into the inner chamber, and a second door providing access to the instrument lock.

5. The surgical isolator of claim 4 in which the instrument lock is further provided with a side having an opening and an open ended sleeve having one end attached to the side around the opening to allow medical personnel to extend a hand through the sleeve into the instrument lock, the sleeve having an elastic band urging the open end closed to restrict the flow of air from the instrument lock.

6. The surgical isolator of claim 1 in which the inner enclosure comprises a first and second side wall and an end wall, the end wall connected to the exhaust line.

7. The surgical isolator of claim 1 further comprising an air handling unit comprising a housing divided by a separation plate into an evacuation compartment and a supply compartment, the evacuation compartment having an air inlet connected to means for neutralizing the presence of live cellular and active viral matter, means for ionizing neutralized particulate matter, an evacuation filter for trapping ionized particulate matter connected to the evacuation blower and an air discharge outlet, the supply compartment having an air-make up inlet and supply filter connected to the supply blower for filtering the filtered air and ambient air, and the separator plate having a recirculating air control valve for controlling the flow of filtered evacuated air into the air supply compartment.

8. The surgical isolator of claim 7, in which the evacuation and supply filters of the air handling assembly are high efficiency particle air filters capable of containing submicron sized particles.

9. The surgical isolator of claim 7, in which the neutralizing means comprises a U-shaped chamber having an ultraviolet lamp around which evacuated air is drawn.

10. The surgical isolator of claim 7 in which the neutralizing means comprises a chamber having a solution containing a biocide/virucide through which the evacuated air is drawn.

11. Method of isolating a surgical field and any air-borne contaminants generated during a procedure in that field, the method comprising the steps of:

(a) placing a first barrier around the surgical field of the procedure to create an inner chamber around the wound site;

(b) enveloping the first barrier in a second barrier to create an outer chamber around the inner chamber;

(c) providing fluid communication between the inner and outer chambers;

(d) evacuating the inner chamber;

(e) neutralizing any live cellular and active viral matter and filtering particulate matter from the air evacuated from the inner chamber; and (f) introducing air into the outer chamber.

12. The method of claim 11 in which live cellular and viral matter is neutralized by irradiating the matter with ultraviolet radiation.

13. The method of claim 11 in which live cellular and viral matter is neutralized by bubbling the matter through a solution containing a biocide/virucide.

14. The method of claim 11, wherein air is introduced into the outer chamber simultaneously as the inner chamber is evacuated.

15. The method of claim 11, further comprising the step of recirculating a portion of the neutralized and filtered air into the outer chamber.

16. A surgical isolator for protecting the patient and medical personnel from contaminants produced during a surgical procedure, comprising:

an inner enclosure adapted to be positioned around the surgical site to form an inner chamber;

an outer enclosure surrounding the inner enclosure forming an outer chamber;

a plurality of openings in the inner and outer enclosures, each opening in the outer enclosure being aligned with an opening in the inner enclosure and having resilient means to restrict the flow of air;

air drawing means connected to the inner enclosure for drawing air out of the inner chamber for producing negative pressure in the inner chamber for keeping contaminants from the inner chamber from entering the outer chamber; and air introducing means connected to the outer enclosure for introducing air into the outer chamber.

17. The surgical isolator of claim 16, further comprising air filtering means connected to the air drawing means for filtering the air drawn from the inner chamber.

18. The surgical isolator of claim 17, wherein the filtering means is connected to the means for introducing filtered air into the outer chamber.

19. The surgical isolator of claim 16, wherein the air drawing means is an exhaust fan.

20. The surgical isolator of claim 16, wherein the means for introducing air into the outer chamber is a supply blower.

* * * * *

UNITED STATES PATENT AND TRADEMARK OFFICE
CERTIFICATE OF CORRECTION

PATENT NO. : 5,728,041
DATED      : March 17, 1998
INVENTOR(S): James M. Fowler, Jr.

It is certified that error appears in the above-indentified patent and that said Letters Patent is hereby corrected as shown below:

```
Col. 1, line 32, cancel "air" (second occurrence);
Col. 1, line 50, change "increasing" to --increasingly--;
Col. 2, line 28, after "clean" insert --air--;
Col. 5, line  1, change "other" to --another--;
Col. 5, line 27, change "24s" to --24a--;
Col. 5, line 54, change "provide" to --provided--;
Col. 6, line  3, change "though" to -- through--;
Col. 7, line 17, cancel "end" (first occurrence).
```

Signed and Sealed this

Twenty-sixth Day of May, 1998

Attest:

BRUCE LEHMAN

Attesting Officer

Commissioner of Patents and Trademarks